United States Patent
Kishimoto et al.

(10) Patent No.: US 7,229,812 B2
(45) Date of Patent: Jun. 12, 2007

(54) MODIFIED SARCOSINE OXIDASE, PROCESS FOR PRODUCING THE SAME AND REAGENT COMPOSITION USING THE SAME

(75) Inventors: Takahide Kishimoto, Tsuruga (JP); Atsushi Sogabe, Tsuruga (JP); Masanori Oka, Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 10/534,583

(22) PCT Filed: Nov. 13, 2003

(86) PCT No.: PCT/JP03/14423

§ 371 (c)(1),
(2), (4) Date: May 11, 2005

(87) PCT Pub. No.: WO2004/044193

PCT Pub. Date: May 27, 2004

(65) Prior Publication Data

US 2006/0051832 A1   Mar. 9, 2006

(30) Foreign Application Priority Data

Nov. 13, 2002  (JP) .............................. 2002-329427
Nov. 13, 2002  (JP) .............................. 2002-329428
Feb. 12, 2003  (JP) .............................. 2003-033641

(51) Int. Cl.
*C12Q 1/26* (2006.01)
*C07H 21/04* (2006.01)
*C12N 9/06* (2006.01)
*C12P 21/06* (2006.01)

(52) U.S. Cl. ............... 435/191; 435/25; 435/320.1; 435/69.1; 435/325; 536/23.2

(58) Field of Classification Search ............. None
See application file for complete search history.

(56) References Cited

U.S. PATENT DOCUMENTS 6,228,626 B1  5/2001  Ichikawa et al.
6,958,231 B2 * 10/2005  Shao et al. ............... 435/227

FOREIGN PATENT DOCUMENTS

DE   3827168 A1    2/1989
DE   19960271 A1   7/2000
JP   07-163341 A   6/1995
JP   07-170976 A   7/1995
JP   10-248572 A   9/1998
JP   10248572    * 9/1998
JP   2001-120273 A 5/2001

OTHER PUBLICATIONS

Yoshiaki et al. (Febs letter 1998, 48, 263-266).*
Database WPINDEX, Thomson Corp. on STN, Accession No. 1995-260034 (English Abstract of JP 07-163341, published Jun. 27, 1995).
Database WPINDEX, Thomson Corp. on STN, Accession No. 1995-271452 (English Abstract of JP 07-170976, published Jul. 11, 1995).
Database WPINDEX, Thomson Corp. on STN, Accession No. 1998-560724 (English Abstract of JP 10-248572, published Sep. 22, 1998).
Database WPINDEX, Thomson Corp. on STN, Accession No. 2001-372962 (English Abstract of JP 2001-120273, published May 8, 2001).
Nishiya et al., *Applied and Environmental Microbiology*, 60(11): 4213-4215 (Nov. 1994).
Nishiya et al., *Applied and Environmental Microbiology*, 61(1): 367-370 (Jan. 1995).
Nishiya et al., *Applied and Environmental Microbiology*, 62(7): 2405-2410 (Jul. 1996).
Nishiya, *Protein Expression and Purification*, 20: 95-97 (2000).
Wagner et al., *Biochemistry*, 39: 8813-8824 (2000).
Zhao et al., *Biochemistry*, 41: 9751-9764 (2002).

* cited by examiner

*Primary Examiner*—Rebecca E Prouty
*Assistant Examiner*—M. Y. Meah
(74) *Attorney, Agent, or Firm*—Leydig, Voit & Mayer, Ltd.

(57) ABSTRACT

A protein having been modified by addition, deletion, insertion or substitution of at least one amino acid in an amino acid sequence constituting a protein having a sarcosine oxidase activity and still having the sarcosine oxidase activity, characterized by having an improved stability in the state of a liquid compared with the unmodified one and/or having a lowered action on L-proline compared with the unmodified one. A sarcosine oxidase having at least one of the following characteristics, i.e., an action on L-proline being 0.7% or less based on sarcosine and a Km value to L-proline being 150 mM or more, when measured at 37° C. and pH 8.0; a process for producing sarcosine oxidase having an excellent substrate specificity which comprises culturing a microorganism capable of producing sarcosine oxidase and collecting the sarcosine oxidase from the culture medium; and a reagent for measuring creatinine which contains the sarcosine oxidase.

19 Claims, No Drawings

SEQUENCE LISTING

<160> NUMBER OF SEQ ID NOS: 14

<210> SEQ ID NO 1
<211> LENGTH: 389
<212> TYPE: PRT
<213> ORGANISM: Arthrobacter SP. TE1826

<400> SEQUENCE: 1

```
Met Ser Ile Lys Lys Asp Tyr Asp Val Ile Val Gly Ala Gly Ser
1               5                   10                  15

Met Gly Met Ala Ala Gly Tyr Tyr Leu Ser Lys Gln Gly Val Lys Thr
                20                  25                  30

Leu Leu Val Asp Ser Phe His Pro His Thr Asn Gly Ser His His
            35                  40                  45

Gly Asp Thr Arg Ile Ile Arg His Ala Tyr Gly Glu Gly Arg Glu Tyr
        50                  55                  60

Val Pro Phe Ala Leu Arg Ala Gln Glu Leu Trp Tyr Glu Leu Glu Lys
65                  70                  75                  80

Glu Thr His His Lys Ile Phe Thr Lys Thr Gly Val Leu Val Phe Gly
                85                  90                  95

Pro Lys Gly Glu Ala Pro Phe Val Ala Glu Thr Met Glu Ala Ala Lys
                100                 105                 110

Glu His Ser Leu Asp Val Asp Leu Leu Glu Gly Ser Glu Ile Asn Lys
            115                 120                 125

Arg Trp Pro Gly Val Thr Val Pro Glu Asn Tyr Asn Ala Ile Phe Glu
        130                 135                 140

Lys Asn Ser Gly Val Leu Phe Ser Glu Asn Cys Ile Arg Ala Tyr Arg
145                 150                 155                 160

Glu Leu Ala Glu Ala Asn Gly Ala Lys Val Leu Thr Tyr Thr Pro Val
                165                 170                 175

Glu Asp Phe Glu Ile Ala Glu Asp Phe Val Lys Ile Gln Thr Ala Tyr
            180                 185                 190

Gly Ser Phe Thr Ala Ser Lys Leu Ile Val Ser Met Gly Ala Trp Asn
        195                 200                 205

Ser Lys Leu Leu Ser Lys Leu Asn Ile Glu Ile Pro Leu Gln Pro Tyr
210                 215                 220

Arg Gln Val Val Gly Phe Phe Glu Cys Asp Glu Lys Lys Tyr Ser Asn
225                 230                 235                 240

Thr His Gly Tyr Pro Ala Phe Met Val Glu Val Pro Thr Gly Ile Tyr
                245                 250                 255

Tyr Gly Phe Pro Ser Phe Gly Gly Cys Gly Leu Lys Ile Gly Tyr His
            260                 265                 270

Thr Tyr Gly Gln Lys Ile Asp Pro Asp Thr Ile Asn Arg Glu Phe Gly
        275                 280                 285

Ile Tyr Pro Glu Asp Glu Gly Asn Ile Arg Lys Phe Leu Glu Thr Tyr
290                 295                 300

Met Pro Gly Ala Thr Gly Glu Leu Lys Ser Gly Ala Val Cys Met Tyr
305                 310                 315                 320

Thr Lys Thr Pro Asp Glu His Phe Val Ile Asp Leu His Pro Gln Phe
                325                 330                 335

Ser Asn Val Ala Ile Ala Ala Gly Phe Ser Gly His Gly Phe Lys Phe
            340                 345                 350

Ser Ser Val Val Gly Glu Thr Leu Ser Gln Leu Ala Val Thr Gly Lys
```

```
                355                 360                 365
Thr Glu His Asp Ile Ser Ile Phe Ser Ile Asn Arg Pro Ala Leu Lys
        370                 375                 380

Gln Lys Glu Thr Ile
385

<210> SEQ ID NO 2
<211> LENGTH: 1167
<212> TYPE: DNA
<213> ORGANISM: Arthrobacter SP. TE1826
<220> FEATURE:
<221> NAME/KEY: CDS
<222> LOCATION: (1)..(1167)
<223> OTHER INFORMATION:

<400> SEQUENCE: 2 atg agt att aaa aaa gat tat gat gta att gtg gtt ggc gct ggt tcc      48
Met Ser Ile Lys Lys Asp Tyr Asp Val Ile Val Val Gly Ala Gly Ser
1               5                   10                  15 atg gga atg gca gct ggg tac tat ctg tct aaa caa ggt gtt aaa aca      96
Met Gly Met Ala Ala Gly Tyr Tyr Leu Ser Lys Gln Gly Val Lys Thr
                20                  25                  30 cta ttg gta gat tca ttt cat cct ccc cat aca aat ggc agc cat cat     144
Leu Leu Val Asp Ser Phe His Pro Pro His Thr Asn Gly Ser His His
            35                  40                  45 ggc gat aca cgg atc att cgt cac gca tat ggc gaa gga aga gag tat     192
Gly Asp Thr Arg Ile Ile Arg His Ala Tyr Gly Glu Gly Arg Glu Tyr
        50                  55                  60 gta ccg ttt gcc ttg aga gca caa gag tta tgg tat gaa tta gaa aag     240
Val Pro Phe Ala Leu Arg Ala Gln Glu Leu Trp Tyr Glu Leu Glu Lys
65                  70                  75                  80 gag act cat cat aaa ata ttt aca aaa aca ggt gta ctc gtt ttt ggt     288
Glu Thr His His Lys Ile Phe Thr Lys Thr Gly Val Leu Val Phe Gly
                85                  90                  95 cct aaa gga gaa gct cct ttc gtt gcc gaa aca atg gaa gcc gca aag     336
Pro Lys Gly Glu Ala Pro Phe Val Ala Glu Thr Met Glu Ala Ala Lys
                100                 105                 110 gaa cat tca tta gat gtt gat tta cta gaa gga agt gaa ata aat aag     384
Glu His Ser Leu Asp Val Asp Leu Leu Glu Gly Ser Glu Ile Asn Lys
            115                 120                 125 cgt tgg cca ggt gta acg gtt cct gag aat tat aat gct att ttt gaa     432
Arg Trp Pro Gly Val Thr Val Pro Glu Asn Tyr Asn Ala Ile Phe Glu
        130                 135                 140 aaa aat tct ggt gtc tta ttt agt gaa aat tgt att cgc gct tac cgt     480
Lys Asn Ser Gly Val Leu Phe Ser Glu Asn Cys Ile Arg Ala Tyr Arg
145                 150                 155                 160 gaa ttg gcg gaa gca aat ggt gcg aaa gtt cta acg tac aca ccc gtt     528
Glu Leu Ala Glu Ala Asn Gly Ala Lys Val Leu Thr Tyr Thr Pro Val
                165                 170                 175 gaa gat ttc gag att gcc gag gac ttc gtc aaa atc caa acc gcc tat     576
Glu Asp Phe Glu Ile Ala Glu Asp Phe Val Lys Ile Gln Thr Ala Tyr
                180                 185                 190 ggc tcc ttt aca gcc agt aaa tta att gtt agc atg ggc gct tgg aat     624
Gly Ser Phe Thr Ala Ser Lys Leu Ile Val Ser Met Gly Ala Trp Asn
            195                 200                 205 agc aaa ctg cta tca aaa tta aat att gaa atc cca ttg cag cca tac     672
Ser Lys Leu Leu Ser Lys Leu Asn Ile Glu Ile Pro Leu Gln Pro Tyr
        210                 215                 220 cgt caa gtt gtc gga ttc ttc gaa tgt gat gaa aaa aaa tat agc aat     720
Arg Gln Val Val Gly Phe Phe Glu Cys Asp Glu Lys Lys Tyr Ser Asn
225                 230                 235                 240
```

```
aca cat ggt tat ccg gcg ttc atg gtc gaa gtc cca act ggc atc tat      768
Thr His Gly Tyr Pro Ala Phe Met Val Glu Val Pro Thr Gly Ile Tyr
            245                 250                 255 tac gga ttt cca agc ttc ggc ggc tgc ggc ttg aaa ata ggc tat cat      816
Tyr Gly Phe Pro Ser Phe Gly Gly Cys Gly Leu Lys Ile Gly Tyr His
            260                 265                 270 acg tat ggt caa aaa atc gat cca gat acg att aat cgt gaa ttt ggt      864
Thr Tyr Gly Gln Lys Ile Asp Pro Asp Thr Ile Asn Arg Glu Phe Gly
            275                 280                 285 att tac ccg gag gat gaa ggg aat att cgc aaa ttc ctg gaa aca tat      912
Ile Tyr Pro Glu Asp Glu Gly Asn Ile Arg Lys Phe Leu Glu Thr Tyr
        290                 295                 300 atg ccg gga gca acc ggc gaa tta aaa agt ggg gca gtt tgc atg tac      960
Met Pro Gly Ala Thr Gly Glu Leu Lys Ser Gly Ala Val Cys Met Tyr
305                 310                 315                 320 aca aaa aca cct gat gag cat ttc gtg att gat tta cat cct caa ttc     1008
Thr Lys Thr Pro Asp Glu His Phe Val Ile Asp Leu His Pro Gln Phe
            325                 330                 335 tcg aat gtc gcg att gca gcc gga ttc tcc gga cat ggg ttt aaa ttc     1056
Ser Asn Val Ala Ile Ala Ala Gly Phe Ser Gly His Gly Phe Lys Phe
            340                 345                 350 tca agc gta gtt ggt gaa aca tta agt caa tta gct gta acc ggt aaa     1104
Ser Ser Val Val Gly Glu Thr Leu Ser Gln Leu Ala Val Thr Gly Lys
            355                 360                 365 aca gaa cac gat att tcc atc ttt tca atc aat cgc cct gct tta aaa     1152
Thr Glu His Asp Ile Ser Ile Phe Ser Ile Asn Arg Pro Ala Leu Lys
        370                 375                 380 caa aaa gaa acg att                                                  1167
Gln Lys Glu Thr Ile
385

<210> SEQ ID NO 3
<211> LENGTH: 38
<212> TYPE: DNA
<213> ORGANISM: Artificial Sequence
<220> FEATURE:
<223> OTHER INFORMATION: Arthrobacter SP. TE1826

<400> SEQUENCE: 3
gactcatcat aaatattta caagaacagg tgtactcg                             38

<210> SEQ ID NO 4
<211> LENGTH: 36
<212> TYPE: DNA
<213> ORGANISM: Artificial Sequence
<220> FEATURE:
<223> OTHER INFORMATION: Arthrobacter SP. TE1826

<400> SEQUENCE: 4
gtgtcttatt tagtgaaaat attattcgcg cttacc                              36

<210> SEQ ID NO 5
<211> LENGTH: 36
<212> TYPE: DNA
<213> ORGANISM: Artificial Sequence
<220> FEATURE:
<223> OTHER INFORMATION: Arthrobacter SP. TE1826

<400> SEQUENCE: 5
gaattggcgg aagcaaaagg tgcgaaagtt ctaacg                              36

<210> SEQ ID NO 6
```

```
<211> LENGTH: 38
<212> TYPE: DNA
<213> ORGANISM: Artificial Sequence
<220> FEATURE:
<223> OTHER INFORMATION: Arthrobacter SP. TE1826

<400> SEQUENCE: 6
gccagtaaat taattgttag cgcgggcgct tggaatag                               38

<210> SEQ ID NO 7
<211> LENGTH: 38
<212> TYPE: DNA
<213> ORGANISM: Artificial Sequence
<220> FEATURE:
<223> OTHER INFORMATION: Arthrobacter SP. TE1826

<400> SEQUENCE: 7
gaatagcaaa ctgctaccaa aattaaatat tgaaatcc                               38

<210> SEQ ID NO 8
<211> LENGTH: 36
<212> TYPE: DNA
<213> ORGANISM: Artificial Sequence
<220> FEATURE:
<223> OTHER INFORMATION: Arthrobacter SP. TE1826

<400> SEQUENCE: 8
gtcggattct tcgaaagcga tgaaaaaaaa tatagc                                 36

<210> SEQ ID NO 9
<211> LENGTH: 38
<212> TYPE: DNA
<213> ORGANISM: Artificial Sequence
<220> FEATURE:
<223> OTHER INFORMATION: Arthrobacter SP. TE1826

<400> SEQUENCE: 9
gtgatgaaaa aaaatatagc tatacacatg gttatccg                               38

<210> SEQ ID NO 10
<211> LENGTH: 33
<212> TYPE: DNA
<213> ORGANISM: Artificial Sequence
<220> FEATURE:
<223> OTHER INFORMATION: Arthrobacter SP. TE1826

<400> SEQUENCE: 10
ccggcgttca tggtccaggt cccaactggc atc                                    33

<210> SEQ ID NO 11
<211> LENGTH: 37
<212> TYPE: DNA
<213> ORGANISM: Artificial Sequence
<220> FEATURE:
<223> OTHER INFORMATION: Arthrobacter SP. TE1826

<400> SEQUENCE: 11
gaaacattaa gtcaattagt tgtaaccggt aaaacag                                37

<210> SEQ ID NO 12
<211> LENGTH: 36
<212> TYPE: DNA
<213> ORGANISM: Artificial Sequence
<220> FEATURE:
<223> OTHER INFORMATION: Arthrobacter SP. TE1826

<400> SEQUENCE: 12
```

```
caaaaacagg tgtactcggt tttggtccta aaggag                                    36

<210> SEQ ID NO 13
<211> LENGTH: 37
<212> TYPE: DNA
<213> ORGANISM: Artificial Sequence
<220> FEATURE:
<223> OTHER INFORMATION: Arthrobacter SP. TE1826

<400> SEQUENCE: 13
gtttgcatgt acacaagaac acctgatgag catttcg                                   37

<210> SEQ ID NO 14
<211> LENGTH: 37
<212> TYPE: DNA
<213> ORGANISM: Artificial Sequence
<220> FEATURE:
<223> OTHER INFORMATION: Arthrobacter SP. TE1826

<400> SEQUENCE: 14
ccagtaaatt aattgttagc gcgggcgctt ggaatag                                   37
```

MODIFIED SARCOSINE OXIDASE, PROCESS FOR PRODUCING THE SAME AND REAGENT COMPOSITION USING THE SAME

TECHNICAL FIELD

The present invention relates to sarcosine oxidase obtained by modifying a protein having a sarcosine oxidase activity by a protein engineering technique, characterized by having an improved stability in the state of a liquid, an excellent substrate specificity and a lowered action on proline, as well as a process for producing sarcosine oxidase and a reagent composition by the use thereof.

BACKGROUND ART

Sarcosine oxidase (EC 1.5.3.1) is used as an enzyme for measuring creatine and creatinine in the body fluid, which are clinical indicators of diagnosis of muscular diseases and renal diseases, together with the other enzymes such as creatininase, creatinase and peroxidase. Sarcosine oxidase acts on sarcosine which is a substrate in the presence of water and oxygen to produce glycine, formaldehyde and hydrogen peroxide.

It has been known that such sarcosine oxidase is produced by bacteria belonging to genera *Bacillus* (JP-54-52789-A, JP-61-162174-A), *Corynebacterium* (J. Biochem., 89:599, 1981), *Cylindrocarpon* (JP-56-92790-A), *Pseudomonas* (JP-60-43379-A), and *Arthrobacter* (JP-2-265478-A). Technology to produce sarcosine oxidase on a large scale using a host such as *Escherichia coli* with a sarcosine oxidase gene obtained from these bacteria by a gene engineering technique has been also reported (JP-5-115281-A, JP-6-113840-A, JP-8-238087-A).

Along with recent liquefied reagents for clinical diagnosis, various stabilization methods of reagent components in a liquid have been investigated, and also for sarcosine oxidase used for reagents for measuring creatinine and creatine, one which is excellent in stability in the liquid has been desired. Our group previously reported a mutant type of sarcosine oxidase whose stability for metal ions was improved by modifying a wild type of sarcosine oxidase in a protein engineering manner (see e.g., JP-7-163341), but concerning long term storage stability in a diagnostic reagent, more improvement has been anticipated.

Furthermore, it has been known that conventional sarcosine oxidase also acts on proline which is one amino acid present in blood, and it has been pointed out that this can cause a true or false difference upon measuring creatinine and creatine (Rinsho Kagaku, 20:144–152, 1991; Seibutsu Shiryo Bunseki, 17:332–337, 1994). In order to solve this problem, our group reported sarcosine oxidase having a lowered action on proline by modifying the wild type of sarcosine oxidase in the protein engineering manner (JP-10-248572-A), but the action thereof on sarcosine which is an original substrate has been unclear, and more improvement has been desired.

It is an object of the present invention to provide modified sarcosine oxidase having an improved stability in a liquid.

It is another object of the present invention to provide sarcosine oxidase having a low reactivity to proline and having an excellent substrate specificity.

It is another object of the present invention to provide sarcosine oxidase having a lowered action on proline.

DISCLOSURE OF THE INVENTION

As a result of an extensive study for accomplishing the above objects, the present inventors have found that sarcosine oxidase can be modified to have an improved stability in a liquid or have a lowered action on proline without impairing an action on sarcosine.

Furthermore, the present inventors have found that sarcosine oxidase can be modified to keep high affinity with sarcosine and have the lowered action on L-proline, and thereby completed the present invention.

That is, the present invention is composed of the following constitution.

[1] Modified sarcosine oxidase which is a protein converted by adding, deleting, inserting or substituting at least one amino acid in an amino acid sequence constituting a protein having a sarcosine oxidase activity, characterized by having the sarcosine oxidase activity and having an improved stability in a liquid compared with one before conversion.

[2] The modified sarcosine oxidase according to [1] characterized in that at least one amino acid in the amino acid sequence constituting the protein having the sarcosine oxidase activity is substituted with other amino acid.

[3] The modified sarcosine oxidase according to [1] wherein the protein having the sarcosine oxidase activity has homology of 50% or more to the amino acid sequence according to SEQ ID NO:1.

[4] The modified sarcosine oxidase according to [1] wherein the protein having the sarcosine oxidase activity has homology of 80% or more to the amino acid sequence according to SEQ ID NO:1.

[5] The modified sarcosine oxidase according to [1] wherein the protein having the sarcosine oxidase activity has the amino acid sequence according to SEQ ID NO:1.

[6] The modified sarcosine oxidase according to [1] characterized in that at least one amino acid in a region corresponding to positions 155 to 250 in the amino acid sequence according to SEQ ID NO:1 is substituted with other amino acid.

[7] The modified sarcosine oxidase according to [1] characterized in that at least one amino acid in a region corresponding to positions 82 to 92 or 354 to 366 in the amino acid sequence according to SEQ ID NO:1 is substituted with other amino acid.

[8] The modified sarcosine oxidase according to [1] characterized in that at least one amino acid selected from the group consisting of regions corresponding to positions 89, 155, 166, 204, 213, 233, 240, 250 and 364 in the amino acid sequence according to SEQ ID NO:1 is substituted with other amino acid.

[9] The modified sarcosine oxidase according to [1] characterized in that lysine at position 89 in the amino acid sequence according to SEQ ID NO:1 is substituted with arginine.

[10] The modified sarcosine oxidase according to [1] characterized in that cysteine at position 155 in the amino acid sequence according to SEQ ID NO:1 is substituted with isoleucine.

[11] The modified sarcosine oxidase according to [1] characterized in that asparagine at position 166 in the amino acid sequence according to SEQ ID NO:1 is substituted with lysine.

[12] The modified sarcosine oxidase according to [1] characterized in that methionine at position 204 in the amino acid sequence according to SEQ ID NO:1 is substituted with alanine.

[13] The modified sarcosine oxidase according to [1] characterized in that serine at position 213 in the amino acid sequence according to SEQ ID NO:1 is substituted with proline.

[14] The modified sarcosine oxidase according to [1] characterized in that cysteine at position 233 in the amino acid sequence according to SEQ ID NO:1 is substituted with serine.

[15] The modified sarcosine oxidase according to [1] characterized in that asparagine at position 240 in the amino acid sequence according to SEQ ID NO:1 is substituted with tyrosine.

[16] The modified sarcosine oxidase according to [1] characterized in that glutamic acid at position 250 in the amino acid sequence according to SEQ ID NO:1 is substituted with glutamine.

[17] The modified sarcosine oxidase according to [1] characterized in that alanine at position 364 in the amino acid sequence according to SEQ ID NO:1 is substituted with valine.

[18] Modified sarcosine oxidase which is a protein converted by adding, deleting, inserting or substituting at least one amino acid in an amino acid sequence constituting a protein having a sarcosine oxidase activity, characterized by having the sarcosine oxidase activity and having a lowered action on L-proline compared with one before conversion.

[19] The modified sarcosine oxidase according to [18] characterized in that at least one amino acid in the amino acid sequence constituting the protein having the sarcosine oxidase activity is substituted with other amino acid.

[20] The modified sarcosine oxidase according to [18] wherein the protein having the sarcosine oxidase activity has homology of 50% or more to the amino acid sequence according to SEQ ID NO:1.

[21] The modified sarcosine oxidase according to [18] wherein the protein having the sarcosine oxidase activity has homology of 80% or more to the amino acid sequence according to SEQ ID NO:1.

[22] The modified sarcosine oxidase according to [18] wherein the protein having the sarcosine oxidase activity has the amino acid sequence according to SEQ ID NO:1.

[23] The modified sarcosine oxidase according to [18] characterized in that at least one amino acid at positions 82 to 152 and 216 to 328 in the amino acid sequence according to SEQ ID NO:1 is substituted with other amino acid.

[24] The modified sarcosine oxidase according to [18] characterized in that at least one amino acid at positions 82 to 97 and 313 to 328 in the amino acid sequence according to SEQ ID NO:1 is substituted with other amino acid.

[25] The modified sarcosine oxidase according to [18] characterized in that at least one amino acid selected from the group consisting of positions 89, 94 and 322 in the amino acid sequence according to SEQ ID NO:1 is substituted with other amino acid.

[26] The modified sarcosine oxidase according to [18] characterized in that lysine at position 89 in the amino acid sequence according to SEQ ID NO:1 is substituted with arginine.

[27] The modified sarcosine oxidase according to [18] characterized in that valine at position 94 in the amino acid sequence according to SEQ ID NO:1 is substituted with glycine.

[28] The modified sarcosine oxidase according to [18] characterized in that lysine at position 322 in the amino acid sequence according to SEQ ID NO:1 is substituted with arginine.

[29] The modified sarcosine oxidase according to [18] characterized in that a Km value for sarcosine after the modification is within 3 times compared with the unmodified one.

[30] The modified sarcosine oxidase according to [18] characterized in that a Km value for sarcosine after the modification is within 1.5 times compared with the unmodified one.

[31] Sarcosine oxidase characterized by having at least one of the following characteristics under a measurement condition at 37° C. and pH 8.0:
  action on L-proline: 0.7% or less based on sarcosine; and
  Km value for L-proline: 150 mM or more.

[32] The sarcosine oxidase according to [31] characterized by having at least one of the following characteristics under a measurement condition at 37° C. and pH 8.0:
  action on L-proline: 0.5% or less based on sarcosine; and
  Km value for L-proline: 200 mM or more.

[33] The sarcosine oxidase according to [31] wherein the Km value for sarcosine is 10 mM or less.

[34] The sarcosine oxidase according to [31] wherein the Km value for sarcosine is 5 mM or less.

[35] A gene encoding the modified sarcosine oxidase according to any one of [1] to [17] and [18] to [30].

[36] A vector containing the gene according to [35].

[37] A transformant transformed with the vector according to [36].

[38] A process for producing modified sarcosine oxidase characterized in that the transformant according to [37] is cultured and the sarcosine oxidase is collected from the culture.

[39] A process for producing modified sarcosine oxidase which is excellent in substrate specificity, characterized in that a microorganism having a production capacity of the sarcosine oxidase according to any one of [31] to [34] is cultured and the sarcosine oxidase is collected from the culture.

[40] A reagent for measuring creatine containing the sarcosine oxidase according to any one of [1] to [17], [18] to [30] and [31] to [34].

[41] A reagent for measuring creatinine containing the sarcosine oxidase according to any one of [1] to [17], [18] to [30] and [31] to [34].

The present invention will be described in detail below.

The modified sarcosine oxidase of the present invention is useful for analysis of creatine and creatinine in the clinical examination field.

One embodiment of the present invention is a protein modified by addition, deletion, insertion or substitution of at least one amino acid in an amino acid sequence constituting a protein having a sarcosine oxidase activity, and modified sarcosine oxidase characterized by having the sarcosine oxidase activity, an improved stability in a liquid compared with an unmodified one, a sufficiently lowered action on proline compared with sarcosine which is an original substrate, or having the sarcosine oxidase activity and a lowered action on proline compared with the unmodified one.

The action on proline can be obtained by a relative ratio (%) of an enzymatic activity using L-proline as the substrate to an enzymatic activity using sarcosine as the substrate. In the sarcosine oxidase of the present invention, the action on L-proline is 0.7% or less and preferably 0.5% or less based on the action on sarcosine.

In another embodiment of the present invention, the sarcosine oxidase has a high Km value (Michaelis-Menten constant) for proline, and is unlikely to be affected by proline in a sample when applied to a reagent for measuring creatinine and creatine. The sarcosine oxidase of the present invention has the Km value of 150 mM or more and preferably 200 mM or more for L-proline.

In another embodiment of the present invention, the sarcosine oxidase of the present invention has the Km value of preferably 10 mM or less and more preferably 5 mM or less for sarcosine in terms of suppressing a necessary amount to be added in the measurement reagent and taking advantage of the high substrate specificity.

The sarcosine oxidase of the present invention is not particularly limited as long as it has the above characters. For example, enzymes derived from microorganisms and mammals can be used. Enzymes obtained by modifying the publicly known sarcosine oxidase using gene engineering/protein engineering technology and enzymes whose property is improved by chemical modification are also included.

The modified sarcosine oxidase in one embodiment of the present invention is characterized in that the stability in the liquid is further improved compared with the unmodified one. The stability in the liquid in the present invention means, for example, a proportion of a residual enzyme activity after the modified enzyme has been dissolved in an appropriate buffer and stored at an appropriate temperature for a certain time period.

The "appropriate buffer" is not particularly limited as long as a type thereof and the temperature is selected so that sufficient buffer capacity is kept at pH of around 7 to 8 which is an optimal pH of the sarcosine oxidase. Preferably, 50 mM potassium phosphate buffer (pH 7.5) or 50 mM PIPES-NaOH buffer (pH 7.5) is selected. Furthermore, surfactants, salts, chelating agents and preservatives may be contained in the buffer if necessary.

A condition of "storage at the appropriate temperature for the certain time period" is not particularly limited, but preferably, a condition of an acceleration (harshness) test is selected with long term storage stability in a liquid diagnostic reagent in mind. Specifically, "storage at 40° C. for 3 days" or "storage at 60° C. for 30 min" is included. When time permits, the storage under a cooling condition at 2 to 10° C. commonly used as the temperature at which the liquid diagnostic drug is actually stored for a long time, for 6 months or more may be selected.

A concentration of the sarcosine oxidase in the storage is not particularly limited, and the concentration of 1 to 30 U/mL is preferably selected on the assumption of the concentration typically used for the diagnostic reagent. More preferably, the concentration of 5 to 20 U/mL is selected.

The "stability being further improved compared with the unmodified one" refers to that an activity keeping proportion after the storage for the certain period is higher than an activity keeping proportion of an unmodified enzyme when measured under the same condition.

One embodiment of the present invention is modified sarcosine oxidase where a residual enzyme activity proportion after storing in 50 mM potassium phosphate buffer (pH 7.5) at 60° C. for 30 min is improved compared with the unmodified one. Another embodiment is the modified sarcosine oxidase where the residual enzyme activity proportion after storing in 50 mM PIPES-NaOH buffer (pH 7.5) containing 2 mM EDTA, 50 mM NaCl, 0.1% (w/v) 2-methylisothiazolone, and 0.1% (w/v) TritonX-100 at 40° C. for 3 days is improved compared with the unmodified one.

The modified sarcosine oxidase in one embodiment of the present invention is characterized in that a reactivity to proline is lowered compared with the unmodified one. The reactivity to proline means the relative ratio of the enzyme activity using proline as the substrate to the enzyme activity using sarcosine which is the original substrate as the substrate. And, as long as the reactivity to proline is lowered, even if a specific activity using sarcosine as the substrate is changed, the enzyme is included in the modified sarcosine oxidase of the present invention. In the modified sarcosine oxidase of the present invention, the Km value for sarcosine may be changed, but when applied to the reagent for measuring creatinine and creatine, it causes lowered reactivity, and thus, the Km value for sarcosine is preferably within 3 times, and more preferably within 1.5 times of that before the modification.

Sarcosine oxidase used for the modification of the present invention is not particularly limited, and for example, the sarcosine oxidase derived from bacteria belonging to genera *Bacillus, Pseudomonas* and *Corynebacterium* known publicly can be used.

An example in which sarcosine oxidase (JP-2-265478-A) derived from *Arthrobacter* sp. TE1826 (Accession No. 10637, Fermentation Research Institute, the Agency of Industrial Science and Technology) was modified in a protein engineering manner is shown as one example in the present invention.

The group of the present inventors have successfully isolated a sarcosine oxidase gene from chromosomal DNA extracted from *Arthrobacter* sp. TE1826, determined an entire DNA structure thereof (described in Journal of Fermentation and Bioengineering, Vol. 75, No. 4:239–244, 1999), successfully produced the sarcosine oxidase in transformants at a high density by a gene engineering technique, and enabled to inexpensively supply the sarcosine oxidase with high purity on a large scale (JP-6-113840-A). An amino acid sequence of the sarcosine oxidase from *Arthrobacter* sp. TE1826 is shown in SEQ ID NO:1. A DNA sequence encoding this amino acid sequence is shown in SEQ ID NO:2.

But, the present invention is not limited to the modified sarcosine oxidase having the amino acid sequence described in SEQ ID NO:1, and may be the other modified protein having the sarcosine oxidase activity. Suitable examples of the other protein having the sarcosine oxidase activity include sarcosine oxidase whose three dimensional structure is similar to that of the sarcosine oxidase having the amino acid sequence described in SEQ ID NO:1, and specifically include other proteins having 50% or more homologous amino acid sequence, more preferably 80% or more homologous amino acid sequence, and having the sarcosine oxidase activity. This is based on the respect that enzyme proteins having 50 to 80% or more homology in the amino acid sequence and exhibiting the same catalytic activity are often similar in the three dimensional structure and often have the same amino acid residues involved in the substrate specificity and the same reaction mechanism.

In the modified sarcosine oxidase, as long as the enzyme activity and/or stability which are essence of the enzyme property of the present invention are not impaired, one or more amino acids may be further deleted, substituted or added. Specifically, one which has added a histidine tag at the N- or C-terminus of the amino acid sequence in order to simplify the purification of sarcosine oxidase is exemplified (e.g., "Jikken Igaku" 20:479–482, 2002).

The homology in the amino acid sequences in the present invention can be calculated using publicly known gene analysis software (e.g., Genetyx-win ver. 3, Genetyx Corporation). The homology refers to a percentage of identical amino acid residues in the range having similarity to the amino acid sequence to be compared.

Another embodiment of the present invention is the modified sarcosine oxidase characterized in that at least one amino acid in the amino acid sequence described in SEQ ID NO:1 is substituted with other amino acid, and having the improved stability in the liquid compared with the unmodified one.

Another embodiment of the present invention is the modified sarcosine oxidase characterized in that at least one amino acid in sites corresponding to positions 155 to 250 in the amino acid sequence from *Arthrobacter* sp. TE1826 described in SEQ ID NO:1 or sites corresponding to positions 155 to 250 in the amino acid sequence described in SEQ ID NO:1 in sarcosine oxidase from other than *Arthrobacter* sp. TE1826 is substituted with the other amino acid, and having the improved stability in the liquid compared with the unmodified one.

Another embodiment of the present invention is the modified sarcosine oxidase characterized in that at least one amino acid in sites corresponding to positions 82 to 92 in the amino acid sequence from *Arthrobacter* sp. TE1826 described in SEQ ID NO:1 or sites corresponding to positions 82 to 92 of the amino acid sequence described in SEQ ID NO:1 in sarcosine oxidase from other than *Arthrobacter* sp. TE1826 is substituted with the other amino acid, and having the improved stability in the liquid compared with the unmodified one.

There is a report of the sarcosine oxidase whose three dimensional structure has been demonstrated by X-ray crystal analysis (e.g., "Structure" Vol. 7, No. 3:331–345, 1999). In accordance with the report, the sarcosine oxidase has the homology to the amino acid sequence described in SEQ ID NO:1, and it has been speculated that the sites corresponding to positions 82 to 92 in the amino acid sequence described in SEQ ID NO:1 which is the amino acid sequence of the sarcosine oxidase from *Arthrobacter* sp. TE1826 or the sites corresponding to positions 82 to 92 in the amino acid sequence described in SEQ ID NO:1 in sarcosine oxidase from other than *Arthrobacter* sp. TE1826 constitute a linked site of a catalytic domain and an FAD binding domain of the sarcosine oxidase.

Another embodiment of the present invention is the modified sarcosine oxidase characterized in that at least one amino acid in sites corresponding to positions 354 to 366 presumed to constitute α-helix containing the position 364 in the amino acid sequence from *Arthrobacter* sp. TE1826 described in SEQ ID NO:1 or sites corresponding to positions 354 to 366 in the amino acid sequence described in SEQ ID NO:1 in the sarcosine oxidase from other than *Arthrobacter* sp. TE1826 is substituted with the other amino acid, and having the improved stability in the liquid compared with the unmodified one.

Preferable is the modified sarcosine oxidase where at least one amino acid selected from the group consisting of positions 89, 155, 166, 204, 213, 233, 240, 250 and 364 in the amino acid sequence described in SEQ ID NO:1 or corresponding positions in the other sarcosine oxidase is substituted with the other amino acid.

More preferable is the modified sarcosine oxidase where at least one amino acid selected from the following group is substituted with the other amino acid. The modified sarcosine oxidase where lysine at position 89 is substituted with arginine, cysteine at position 155 is substituted with isoleucine, asparagine at position 166 is substituted with lysine, methionine at position 204 is substituted with alanine, serine at position 213 is substituted with proline, cysteine at position 233 is substituted with serine, asparagine at position 240 is substituted with tyrosine, glutamic acid at position 250 is substituted with glutamine or alanine at position 364 is substituted with valine is exemplified.

Another embodiment of the present invention is the modified sarcosine oxidase where the protein having the sarcosine oxidase activity has the amino acid sequence described in SEQ ID NO:1.

Another embodiment of the present invention is the modified sarcosine oxidase where at least one amino acid in a region which constitutes the catalytic domain and the linked site of the catalytic domain and the FAD binding domain is substituted with the other amino acid. It has been predicted that positions 82 to 152 and positions 216 to 328 in the amino acid sequence described in SEQ ID NO:1 constitute the catalytic domain and the linked site of the catalytic domain and the FAD binding domain of the sarcosine oxidase, from the sarcosine oxidase having the homology to the amino acid sequence described in SEQ ID NO:1, whose three dimensional structure has been demonstrated by the X-ray crystal analysis (e.g., "Structure" Vol. 7, No. 3:331–345, 1999).

Preferable is the modified sarcosine oxidase where at least one amino acid in the region which constitutes the linked site of the catalytic domain and the FAD binding domain, and a β-sheet structure of the catalytic domain proximal thereto is substituted with the other amino acid. It has been predicted that positions 82 to 97 and positions 313 to 328 in the amino acid sequence described in SEQ ID NO:1 constitute the linked site of the catalytic domain and the FAD binding domain, and the β-sheet structure of the catalytic domain proximal thereto of the sarcosine oxidase (e.g., "Structure" Vol. 7, No. 3:331–345, 1999).

Another embodiment of the present invention is the modified sarcosine oxidase where at least one amino acid selected from the group consisting of positions 89, 94 and 322 in the amino acid sequence described in SEQ ID NO:1 is substituted with the other amino acid.

Among them, preferable is the modified sarcosine oxidase where lysine at position 89 is substituted with arginine, valine at position 94 is substituted with glycine or lysine at position 322 is substituted with arginine in the amino acid sequence described in SEQ ID NO:1.

Another embodiment of the present invention is a gene encoding the above modified sarcosine oxidase, a vector containing the gene, a transformant transformed with the vector, and further a process for producing the modified sarcosine oxidase characterized in that the transformant is cultured and the sarcosine oxidase is collected from the culture.

The process for producing the sarcosine oxidase of the present invention is not particularly limited, and when the publicly known enzyme is improved using the protein engineering technique, it is possible to produce by the procedure shown below. As a method for modifying the amino acid sequence which constitutes the protein having the sarcosine oxidase activity, the typically performed technique for modifying gene information is used. That is, a DNA having the gene information of the modified protein is made by converting a certain base of a DNA having the gene information of the protein, or inserting or deleting a certain base. Specific methods for converting the base in the DNA molecule include the use of commercially available kits (Transformer Mutagenesis kit supplied from Clonetech; EXOIII/Mung Bean Deletion Kit supplied from Stratagene; QuickChange Site Directed Mutagenesis Kit supplied from Stratagene) or the utilization of polymerase chain reaction (PCR).

The DNA having the gene information of the produced modified protein is ligated to a plasmid and transfected into a host microorganism, which then becomes a transformant which produces the modified protein. When *Escherichia coli* is used as the host microorganism, pBluescript and pUC18 can be used as the plasmid. As the host microorganism, for example, *Escherichia coli* W3110, *Escherichia coli* C600, *Escherichia coli* JM109, *Escherichia coli* DH5α and the like can be utilized. As the method for transfecting a recombinant vector into the host microorganism, when the host is the microorganism belonging to genus *Escherichia*, it is possible to employ the method in which the recombinant DNA is transfected in the presence of calcium ions, and further, an electroporation method may be used. Furthermore, commercially available competent cells (e.g., Competent High JM109 supplied from Toyobo Co., Ltd.) may be used.

The modified protein can be stably produced on a large scale by culturing the microorganism which is the transformant obtained in this way in a nutrient medium. For a culture form of the microorganism which is the transformant, a culture condition could be selected in consideration of nutritional physiological natures of the host, typically the liquid culture is often performed, but industrially, it is advantageous to perform an aeration stirring culture. As nutritious sources of the medium, those used for the culture of the microorganism can be widely used. Carbon sources may be carbon compounds capable of being utilized, and for example, glucose, sucrose, lactose, maltose, fructose, treacle, pyruvic acid and the like are used. Nitrogen sources may be usable nitrogen compounds, and for example, peptone, meat extract, yeast extract, hydrolyzed casein, alkali extract of soy bean cake, and the like are used. Additionally, phosphate salts, carbonate salts, sulfate salts, salts of magnesium, calcium, potassium, iron, manganese and zinc, certain amino acids, certain vitamins are used if necessary. A culture temperature can be appropriately changed in the range where the bacteria grow and produce the modified protein, and in the case of *Escherichia coli* it is preferably about 20 to 42° C. A culture period is changed more or less depending on the condition, and is typically about 6 to 48 hours because the culture may be appropriately terminated when the modified protein has been yield maximally. Medium pH can be appropriately changed in the range where the bacteria grow and produce the modified protein, and in particular is preferably about pH 6.0 to 9.0.

The sarcosine oxidase can be collected by culturing the microorganism having the sarcosine oxidase of the present invention as a wild type enzyme under the culture condition suitable for growth of each microorganism using an appropriate nutritious medium. At that time, in order to induce the enzyme expression, it is desirable to add sarcosine, creatine and dimethyl glycine at an appropriate amount into the medium.

A culture fluid containing microbial cells which produce the modified protein in the culture can be employed as it is and utilized, but in general, when the modified protein is present in the culture fluid in accordance with standard methods, a modified protein-containing solution is utilized after separating from the microbial cells by filtration, centrifugation and the like. When the modified protein is present in the microbial cells, the microbial cells are collected by means of filtration, centrifugation and the like from the culture, then these microbial cells are disrupted by a mechanical method or an enzymatic method such as lysosome, and if necessary the modified protein is solubilized by adding a chelating agent such as EDTA or a surfactant to separate/collect as an aqueous solution.

The modified protein-containing solution obtained in this way may be precipitated by, for example, concentration under reduced pressure, concentration via a membrane, salting out by ammonium sulfate or sodium sulfate, or fractional precipitation by hydrophilic organic solvent such as methanol, ethanol and acetone. Treatment with heat and treatment taking advantage of isoelectric point are also effective purification means. The purified modified protein can be obtained by gel filtration, adsorption chromatography, ion exchange chromatography or affinity chromatography by an adsorption agent and a gel filtrating agent.

Another embodiment of the present invention is a reagent for measuring creatine or creatinine containing the above modified sarcosine oxidase. In the reagent for measuring creatine or creatinine, an active period of the reagent can be prolonged or measurement accuracy can be enhanced by using the modified sarcosine oxidase having the improved liquid stability and the lowered action on proline. An effect degree of proline can be suppressed to less than 7% and preferably less than 5%.

The reagent for measuring creatine of the present invention includes the modified sarcosine oxidase having the improved stability in the liquid, the small substrate specificity for proline or the lowered reaction to proline, creatine amidinohydrolase, peroxidase and a reagent for detecting hydrogen peroxide.

The reagent for measuring creatinine includes the modified sarcosine oxidase having the improved stability in the liquid, the small substrate specificity for proline or the lowered reaction to proline, creatinine amidohydrolase, creatine amidinohydrolase, peroxidase and a reagent for detecting hydrogen peroxide.

The reagent for detecting hydrogen peroxide is a reagent which measures hydrogen peroxide produced by the sarcosine oxidase as a produced pigment in the presence of peroxidase, and includes an oxidative coloring reagent and if necessary a coupler such as 4-aminoantipyrine and 3-methyl-2-benzothiazolinone.

The reagent for detecting hydrogen peroxide of the present invention is not particularly limited, and various commercially available ones can be used. Furthermore, in the above reagent for measuring creatine or creatinine, metal salts, proteins, amino acids, sugars, organic acids and the like can be also used as stabilizing agents. Preservatives and surfactants are usually added in the range where no harmful effect is given to reagent performance, and used together with an appropriate buffer. One or more are selected for types, concentrations and pH of the buffer depending on the purposes such as storage of each reagent ingredient and enzyme reaction, and when using any buffer, pH at the enzyme reaction is preferably in the range of 5.0 to 10.0.

In the present invention, the sarcosine oxidase activity is measured under the following condition.

<Reagents>
100 mM Tris-HCl buffer (pH 8.0) (containing 200 mM sarcosine and 0.1% Triton X-100)
0.1% 4-aminoantipyrine
0.1% phenol
25 U/mL peroxidase <Measurement Condition>
A reaction mixture is prepared by mixing the above Tris-HCl buffer, 4-aminoantipyrine solution, phenol solution and peroxidase solution at a ratio of 5:1:2:2. The reaction mixture (1 mL) is taken to a test tube, preliminarily warmed at 37° C. for about 5 min, and 0.05 mL of an enzyme solution is added to start the reaction. The reaction at 37° C. is performed accurately for 10 min, then 2.0 mL of an aqueous solution of 0.25% SDS is added to stop the reaction, and an absorbance at 500 nm of this solution is measured. In a blind test, distilled water instead of the enzyme solution is added to the reagent mixture, and the same manipulation is followed to measure the absorbance. Under the above condition, an amount of the enzyme which produces 1 µmol of hydrogen peroxide per min is made one unit. The reactivity to proline was measured as a relative ratio of activities when sarcosine in the above reagent was replaced by L-proline at the same concentration.

In accordance with the present invention, it became possible to supply the modified sarcosine oxidase having the improved liquid stability, the modified sarcosine oxidase having the lowered action on proline, and the modified sarcosine oxidase having the small action on L-proline and the excellent substrate specificity by modifying the protein having the sarcosine oxidase activity by the protein engineering technique. By the use of the modified sarcosine oxidase of the present invention as the enzyme for measuring creatine and creatinine in the body fluid, which are clinical indicators of the diagnosis for muscular diseases and renal diseases, it becomes possible to accurately measure creatine and creatinine without being affected by coexisting substance (e.g., proline), and the liquid stability of the reagent can be improved.

BEST MODE FOR CARRYING OUT THE INVENTION

The present invention will be specifically described with reference to the following Examples, but the invention is not limited thereto.

For example, among 13 types of modified sarcosine oxidases shown in Example 3A and 9 types of modified sarcosine oxidases shown in Example 3B described later, SAOM1 is a mutant where lysine at position 89 is substituted with arginine in the amino acid sequence of SEQ ID NO:1 and SAOM2 is a mutant where valine at position 94 is substituted with glycine in the amino acid sequence of SEQ ID NO:1. However, one or several amino acids may further be deleted, substituted or added within the range where the performance of the mutant is not substantially affected. This is the same for mutants other than SAOM1 and SAOM2.

EXAMPLE 1

Construction of Expression Plasmid for Sarcosine Oxidase

An expression plasmid, pSAOEP3 for sarcosine oxidase derived from *Arthrobacter* sp. TE1826 strain was constructed in accordance with the method described in JP-7-163341-A. This expression plasmid contains an inserted DNA fragment of about 1.7 Kbp containing a gene encoding the sarcosine oxidase of TE1826 at a multiple cloning site of pUC18. A nucleotide sequence thereof is shown in SEQ ID NO:2, and an amino acid sequence of the sarcosine oxidase deduced from the nucleotide sequence is shown in SEQ ID NO:1.

EXAMPLE 2A

Preparation of Modified Sarcosine Oxidase Gene

A recombinant plasmid (pSAOM1A) encoding modified sarcosine oxidase where lysine at position 89 was substituted with arginine in the amino acid sequence of SEQ ID NO:1 was obtained by using the expression plasmid pSAOEP3 containing a sarcosine oxidase gene and a synthetic oligonucleotide in SEQ ID NO:3 and a synthetic oligonucleotide complementary thereto, using Quick-Change™ Site-Directed Mutagenesis Kit (supplied from Stratagene), manipulating in accordance with the protocol, and further sequencing.

A recombinant plasmid (pSAOM2A) encoding modified sarcosine oxidase where cysteine at position 155 was substituted with isoleucine in the amino acid sequence of SEQ ID NO:1 was obtained by using pSAOEP3 and a synthetic oligonucleotide in SEQ ID NO:4 and a synthetic oligonucleotide complementary thereto, using QuickChange™ Site-Directed Mutagenesis Kit (supplied from Stratagene), and manipulating in the same way as in the above.

A recombinant plasmid (pSAOM3A) encoding modified sarcosine oxidase where asparagine at position 166 was substituted with lysine in the amino acid sequence of SEQ ID NO:1 was obtained by using pSAOEP3 and a synthetic oligonucleotide in SEQ ID NO:5 and a synthetic oligonucleotide complementary thereto, and manipulating in the same way as in the above.

A recombinant plasmid (pSAOM4A) encoding modified sarcosine oxidase where methionine at position 204 was substituted with alanine in the amino acid sequence of SEQ ID NO:1 was obtained by using pSAOEP3 and a synthetic oligonucleotide in SEQ ID NO:6 and a synthetic oligonucleotide complementary thereto, and manipulating in the same way as in the above.

A recombinant plasmid (pSAOM5A) encoding modified sarcosine oxidase where serine at position 213 was substituted with proline in the amino acid sequence of SEQ ID NO:1 was obtained by using pSAOEP3 and a synthetic oligonucleotide in SEQ ID NO:7 and a synthetic oligonucleotide complementary thereto, and manipulating in the same way as in the above.

A recombinant plasmid (pSAOM6A) encoding modified sarcosine oxidase where cysteine at position 233 was substituted with serine in the amino acid sequence of SEQ ID NO:1 was obtained by using pSAOEP3 and a synthetic oligonucleotide in SEQ ID NO:8 and a synthetic oligonucleotide complementary thereto, and manipulating in the same way as in the above.

A recombinant plasmid (pSAOM7A) encoding modified sarcosine oxidase where asparagine at position 240 was substituted with tyrosine in the amino acid sequence of SEQ ID NO:1 was obtained by using pSAOEP3 and a synthetic oligonucleotide in SEQ ID NO:9 and a synthetic oligonucleotide complementary thereto, and manipulating in the same way as in the above.

A recombinant plasmid (pSAOM8A) encoding modified sarcosine oxidase where glutamic acid at position 250 was substituted with glutamine in the amino acid sequence of SEQ ID NO:1 was obtained by using pSAOEP3 and a synthetic oligonucleotide in SEQ ID NO:10 and a synthetic oligonucleotide complementary thereto, and manipulating in the same way as in the above.

A recombinant plasmid (pSAOM9A) encoding modified sarcosine oxidase where alanine at position 364 was substituted with valine in the amino acid sequence of SEQ ID NO:1 was obtained by using pSAOEP3 and a synthetic oligonucleotide in SEQ ID NO:11 and a synthetic oligonucleotide complementary thereto, and manipulating in the same way as in the above.

A recombinant plasmid (pSAOM10A) encoding modified sarcosine oxidase where lysine at position 89 was substituted with arginine and serine at position 213 was substituted with proline in the amino acid sequence of SEQ ID NO:1 was obtained by using pSAOM1A and a synthetic oligonucleotide in SEQ ID NO:7 and a synthetic oligonucleotide complementary thereto, and manipulating in the same way as in the above.

A recombinant plasmid (pSAOM11A) encoding modified sarcosine oxidase where lysine at position 89 was substituted with arginine, serine at position 213 was substituted with proline and glutamic acid at position 250 was substituted with glutamine in the amino acid sequence of SEQ ID NO:1 was obtained by using pSAOM10A and a synthetic oligonucleotide in SEQ ID NO:10 and a synthetic oligonucleotide complementary thereto, and manipulating in the same way as in the above.

A recombinant plasmid (pSAOM12A) encoding modified sarcosine oxidase where lysine at position 89 was substituted with arginine, cysteine at position 155 was substituted with isoleucine, asparagine at position 166 was substituted with lysine, serine at position 213 was substituted with proline, glutamic acid at position 250 was substituted with glutamine and alanine at position 364 was substituted with valine in the amino acid sequence of SEQ ID NO:1 was obtained by using pSAOM11A and synthetic oligonucleotides in SEQ ID NOS:4, 5, 11 and synthetic oligonucleotides complementary thereto, and manipulating in the same way as in the above.

A recombinant plasmid (pSAOM13A) encoding modified sarcosine oxidase where lysine at position 89 was substituted with arginine, methionine at position 204 was substituted with alanine, serine at position 213 was substituted with proline, cysteine at position 233 was substituted with serine, asparagine at position 240 was substituted with tyrosine, and glutamic acid at position 250 was substituted with glutamine in the amino acid sequence of SEQ ID NO:1 was obtained by using pSAOM11A and synthetic oligonucleotides in SEQ ID NOS:6, 8, 9 and synthetic oligonucleotides complementary thereto, and manipulating in the same way as in the above.

EXAMPLE 3A

Preparation of Modified Sarcosine Oxidases

Competent cells of *Escherichia coli* JM109 were transformed with each recombinant plasmid of pSAOM1A, pSAOM2A, pSAOM3A, pSAOM4A, pSAOM5A, pSAOM6A, pSAOM7A, pSAOM8A, pSAOM9A, pSAOM10A, pSAOM11A, pSAOM12A, and pSAOM13A to obtain the transformants.

Terrific broth (400 mL) was dispensed in a 2 L Sakaguchi flask, autoclaved at 121° C. for 20 min, cooled, and subsequently ampicillin separately sterilized and filtrated was added at 100 μg/mL. A culture fluid (5 mL) of *Escherichia coli* JM109 (pSAOM1) previously cultured in LB medium containing 100 μg/mL of ampicillin at 30° C. for 16 hours was inoculated to this medium, which was then cultured with aeration and stirring at 30° C. for 20 hours. At the completion of the culture, a sarcosine oxidase activity was about 9.5 U/mL per 1 mL of the culture fluid in the above activity measurement.

The above microbial cells were collected by centrifugation, suspended in 20 mM phosphate buffer (pH 7.5), subsequently disrupted ultrasonically, and further centrifuged to yield a supernatant as a crud enzyme solution. Nucleic acids were removed using polyethyleneimine from the resulting crude enzyme solution, ammonium sulfate fractionation was given thereto, and then separation and purification was performed by dialyzing with 20 mM phosphate buffer (pH 7.5), applying on DEAE Sepharose CL-6B (supplied from Amersham Bioscience) and further treating with heat for one hour to yield a purified enzyme preparation. The preparation obtained by the present method exhibited a nearly single band on SDS-PAGE. This mutant was designated as SAOM1A.

For transformants of *Escherichia coli* JM109 transformed with each recombinant plasmid of pSAOM2A, pSAOM3A, pSAOM4A, pSAOM5A, pSAOM6A, pSAOM7A, pSAOM8A, pSAOM9A, pSAOM10A, pSAOM11A, pSAOM12A, and pSAOM13A, a purified enzyme preparation was obtained by the same way in the above, and the obtained enzyme preparation was each designated as SAOM2A, SAOM3A, SAOM4A, SAOM5A, SAOM6A, SAOM7A, SAOM8A, SAOM9A, SAOM10A, SAOM11A, SAOM12A, and SAOM13A.

COMPARATIVE EXAMPLE 1

Preparation of Wild Type Sarcosine Oxidase

As Comparative Example, *Escherichia coli* JM109 was transformed with pSAOEP3, and for the resulting transformant, a purified preparation of the unmodified enzyme was obtained in the same way as the above.

EXAMPLE 4A

Evaluation of Modified Sarcosine Oxidases 1

Mutant sarcosine oxidases (SAOM1A, SAOM2A, SAOM3A, SAOM4A, SAOM5A, SAOM6A, SAOM7A, SAOM8A) obtained in Example 3A and the sarcosine oxidase obtained in Comparative Example 1 were each added in 50 mM potassium phosphate buffer (pH 7.5) at 5 U/mL, and a proportion (%) of the residual enzyme activity after storing at 60° C. for 30 min was measured. The results are shown in Table 1. As is shown in Table 1, it has been confirmed that the modified sarcosine oxidase of the present invention is improved in liquid stability compared with the unmodified one.

TABLE 1

| Modified one | Mutant | Residual activity ratio (%) |
|---|---|---|
| SAOM1A | K89R | 34 |
| SAOM2A | C155I | 46 |
| SAOM3A | N166K | 37 |
| SAOM4A | M204A | 51 |
| SAOM5A | S213P | 47 |
| SAOM7A | N240Y | 52 |
| SAOM8A | E250Q | 31 |
| Unmodified | — | 19 |

EXAMPLE 4A

Evaluation of Modified Sarcosine Oxidases 2

Mutant sarcosine oxidases (SAOM1A, SAOM2A, SAOM5A, SAOM6A, SAOM7A, SAOM8A SAOM9A) obtained in Example 3A and the sarcosine oxidase obtained in Comparative Example 1 were each added in IPES-NaOH buffer (pH 7.5) containing 2 mM dihydrogen disodium ethylenediamine tetraacetate, 50 mM NaCl, 0.1% (w/v) 2-methylisothiazolone (supplied from Roche Diagnostics) and 0.1% (w/v) Triton X-100 at 5 U/mL, and a proportion (%) of the residual enzyme activity after storing at 40° C. for 3 days was measured. The results are shown in Table 2. As is shown in Table 2, it has been confirmed that the modified sarcosine oxidase of the present invention is improved in liquid stability compared with the unmodified one.

TABLE 2

| Modified one | Mutant | Residual activity ratio (%) |
|---|---|---|
| SAOM1A | K89R | 41 |
| SAOM2A | C155I | 47 |
| SAOM5A | S213P | 49 |
| SAOM6A | C233S | 72 |
| SAOM7A | N240Y | 73 |
| SAOM8A | E250Q | 40 |
| SAOM9A | A364V | 45 |
| Unmodified | — | 30 |

EXAMPLE 5A

Evaluation of Modified Sarcosine Oxidases 3

The stability of mutant sarcosine oxidases (SAOM1A, SAOM10A, SAOM11A, SAOM12A, SAOM13A) obtained in Example 3A and the sarcosine oxidase obtained in Comparative Example 1 in a reagent for measuring creatinine was analyzed. To 50 mM PIPES-NaOH buffer (pH 7.5) containing 1 mM dihydrogen disodium ethylenediamine tetraacetate, 50 mM sodium chloride, 0.1% (w/v) 2-methylisothiazolone (supplied from Roche Diagnostics), 0.1% (w/v) Triton X-100, 0.02% (w/v) 4-aminoantipyrine, 0.02% (w/v) TOOS (supplied from Dojindo Corporate), 100 U/mL creatinine amidinohydrolase (CNH-211, supplied from Toyobo Co., Ltd.), 50 U/mL creatine amidinohydrolase (CRH-221, supplied from Toyobo Co., Ltd.), and 10 U/mL peroxidase (PEO-301, supplied from Toyobo Co., Ltd.), the above sarcosine oxidase was added at 10 U/mL, and stored at 35° C. for 2 weeks, and then a proportion of the residual sarcosine oxidase activity was measured. The results are shown in Table 3. As is shown in Table 3, it has been confirmed that the modified sarcosine oxidase of the present invention is improved in liquid stability in the reagent for measuring creatinine compared with the unmodified one.

TABLE 3

| Modified one | Mutant | Residual activity ratio (%) |
|---|---|---|
| SAOM1A | K89R | 28 |
| SAOM10A | K89R, S213P | 44 |
| SAOM11A | K89R, S213P, E250Q | 51 |
| SAOM12A | K89R, C155I, | 77 |

TABLE 3-continued

| Modified one | Mutant | Residual activity ratio (%) |
|---|---|---|
| SAOM13A | N166K, S213P, E250Q, A364V K89R, M204A, S213P, C233S, N240Y, E250Q | 79 |
| Unmodified | — | 16 |

EXAMPLE 6A

Evaluation of Modified Sarcosine Oxidases 4

The stability of mutant sarcosine oxidases (SAOM1A, SAOM10A, SAOM11A, SAOM12A, SAOM13A) obtained in Example 3A and the sarcosine oxidase obtained in Comparative Example 1 in a reagent for measuring creatine was analyzed. To 50 mM PIPES-NaOH buffer (pH 7.5) containing 1 mM dihydrogen disodium ethylenediamine tetraacetate, 50 mM sodium chloride, 0.1% (w/v) 2-methylisothiazolone (supplied from Roche Diagnostics), 0.1% (w/v) Triton X-100, 0.02% (w/v) 4-aminoantipyrine, 0.02% (w/v) TOOS (supplied from Dojindo Corporate), 50 U/mL creatine amidinohydrolase (CRH-221, supplied from Toyobo Co., Ltd.), and 10 U/mL peroxidase (PEO-301, supplied from Toyobo Co., Ltd.), the above sarcosine oxidase was added at 10 U/mL, and stored at 35° C. for 2 weeks, and then a proportion of the residual sarcosine oxidase activity was measured. The results are shown in Table 3. As is shown in Table 3, it has been confirmed that the modified sarcosine oxidase of the present invention is improved in liquid stability in the reagent for measuring creatine compared with the unmodified one.

TABLE 4

| Modified one | Mutant | Residual activity ratio (%) |
|---|---|---|
| SAOM1A | K89R | 31 |
| SAOM10A | K89R, S213P | 44 |
| SAOM11A | K89R, S213P, E250Q | 52 |
| SAOM12A | K89R, C155I, N166K, S213P, E250Q, A364V | 80 |
| SAOM13A | K89R, M204A, S213P, C233S, N240Y, E250Q | 77 |
| Unmodified (control) | — | 14 |

EXAMPLE 2B

Preparation of Modified Sarcosine Oxidase Gene

A recombinant plasmid (pSAOM1B) encoding modified sarcosine oxidase where lysine at position 89 was substituted with arginine in the amino acid sequence of SEQ ID NO:1 was obtained by using the expression plasmid pSAOEP3 containing a sarcosine oxidase gene and a synthetic oligonucleotide in SEQ ID NO:3 and a synthetic oligonucleotide complementary thereto, using Quick- Change™ Site-Directed Mutagenesis Kit (supplied from Stratagene), manipulating in accordance with the protocol, and further sequencing.

A recombinant plasmid (pSAOM2B) encoding modified sarcosine oxidase where valine at position 94 was substituted with glycine in the amino acid sequence of SEQ ID NO:1 was obtained by using pSAOEP3 and a synthetic oligonucleotide in SEQ ID NO:12 and a synthetic oligonucleotide complementary thereto, using QuickChange™ Site-Directed Mutagenesis Kit (supplied from Stratagene), and manipulating in the same way as in the above.

A recombinant plasmid (pSAOM3B) encoding modified sarcosine oxidase where lysine at position 322 was substituted with arginine in the amino acid sequence of SEQ ID NO:1 has was by using pSAOEP3 and a synthetic oligonucleotide in SEQ ID NO:13 and a synthetic oligonucleotide complementary thereto, and manipulating in the same way as in the above.

A recombinant plasmid (pSAOM4B) encoding modified sarcosine oxidase where valine at position 94 was substituted with glycine and glutamic acid at position 250 was substituted with glutamine in the amino acid sequence of SEQ ID NO:1 was obtained by using pSAOM2B and a synthetic oligonucleotide in SEQ ID NO:10 and a synthetic oligonucleotide complementary thereto, and manipulating in the same way as in the above.

A recombinant plasmid (pSAOM5B) encoding modified sarcosine oxidase where lysine at position 89 was substituted with arginine, valine at position 94 was substituted with glycine and glutamic acid at position 250 was substituted with glutamine in the amino acid sequence of SEQ ID NO:1 was obtained by using pSAOM4B and the synthetic oligonucleotide in SEQ ID NO:3 and the synthetic oligonucleotide complementary thereto, and manipulating in the same way as in the above.

A recombinant plasmid (pSAOM6B) encoding modified sarcosine oxidase where lysine at position 89 was substituted with arginine, valine at position 94 was substituted with glycine, serine at position 213 was substituted with proline and glutamic acid at position 250 was substituted with glutamine in the amino acid sequence of SEQ ID NO:1 was obtained by using pSAOM5B and a synthetic oligonucleotide in SEQ ID NO:7 and a synthetic oligonucleotide complementary thereto, and manipulating in the same way as in the above.

A recombinant plasmid (pSAOM7B) encoding modified sarcosine oxidase where lysine at position 89 was substituted with arginine, valine at position 94 was substituted with glycine, methionine at position 204 was substituted with alanine, serine at position 213 was substituted with proline and glutamic acid at position 250 was substituted with glutamine in the amino acid sequence of SEQ ID NO:1 was obtained by using pSAOM6B and a synthetic oligonucleotide in SEQ ID NO:14 and a synthetic oligonucleotide complementary thereto, and manipulating in the same way as in the above.

A recombinant plasmid (pSAOM8B) encoding modified sarcosine oxidase where lysine at position 89 was substituted with arginine, valine at position 94 was substituted with glycine, asparagine at position 166 was substituted with lysine, methionine at position 204 was substituted with alanine, serine at position 213 was substituted with proline and glutamic acid at position 250 was substituted with glutamine in the amino acid sequence of SEQ ID NO:1 was obtained by using pSAOM7B and a synthetic oligonucleotide in SEQ ID NO:5 and a synthetic oligonucleotide complementary thereto, and manipulating in the same way as in the above.

A recombinant plasmid (pSAOM9B) encoding modified sarcosine oxidase where lysine at position 89 was substituted with arginine, valine at position 94 was substituted with glycine, asparagine at position 166 was substituted with lysine, methionine at position 204 was substituted with alanine, serine at position 213 was substituted with proline, glutamic acid at position 250 was substituted with glutamine, and lysine at position 322 was substituted with arginine in the amino acid sequence of SEQ ID NO:1 was obtained by using pSAOM8B and a synthetic oligonucleotide in SEQ ID NO:13 and a synthetic oligonucleotide complementary thereto, and manipulating in the same way as in the above.

EXAMPLE 3B

Preparation of Modified Sarcosine Oxidases

Competent cells of *Escherichia coli* JM109 were transformed with each recombinant plasmid of pSAOM1B, pSAOM2B, pSAOM3B, pSAOM4B, pSAOM5B, pSAOM6B, pSAOM7B, pSAOM8B, and pSAOM9B to obtain the transformants.

Terrific broth (400 mL) was dispensed in a 2 L Sakaguchi flask, autoclaved at 121° C. for 20 min, cooled, and subsequently ampicillin separately sterilized and filtrated was added at 100 μg/mL. A culture fluid (5 mL) of *Escherichia coli* JM109 (pSAOM1) previously cultured in LB medium containing 100 μg/mL of ampicillin at 30° C. for 16 hours was inoculated to this medium, which was then cultured with aeration and stirring at 30° C. for 20 hours. At the completion of the culture, a sarcosine oxidase activity was about 9.5 U/mL per 1 mL of the culture fluid in the above activity measurement.

The above microbial cells were collected by centrifugation, suspended in 20 mM phosphate buffer (pH 7.5), subsequently disrupted ultrasonically, and further centrifuged to yield a supernatant as a crud enzyme solution. Nucleic acids were removed using polyethyleneimine from the resulting crude enzyme solution, ammonium sulfate fractionation was given thereto, and then separation and purification was performed by dialyzing with 20 mM phosphate buffer (pH 7.5), applying on DEAE Sepharose CL-6B (supplied from Amersham Bioscience) and further treating with heat for one hour to yield a purified enzyme preparation. The preparation obtained by the present method exhibited a nearly single band on SDS-PAGE. This mutant was designated as SAOM1B.

For transformants of *Escherichia coli* JM109 transformed with each recombinant plasmid of pSAOM2B, pSAOM3B, pSAOM4B, pSAOM5B, pSAOM6B, pSAOM7B, pSAOM8B, and pSAOM9B, a purified enzyme preparation was obtained by the same way in the above, and the obtained enzyme preparation was each designated as SAOM2B, SAOM3B, SAOM4B, SAOM5B, SAOM6B, SAOM7B, SAOM8B, and SAOM9B.

EXAMPLE 4B

Evaluation of Modified Sarcosine Oxidases

Various sarcosine oxidases obtained in Example 3B and Comparative Example 1 were evaluated.

Action on proline was calculated from a relative ratio (%) of the enzyme activity using L-proline as the substrate to the enzyme activity suing sarcosine as the substrate in the above activity measurement method. Km values for sarcosine and L-proline were measured by changing the substrate concentration in the above activity measurement method. The results are shown in Table 5.

As is shown in Table 5, it has been confirmed that the reactivity to proline of the modified sarcosine oxidase of the present invention is lowered compared with the unmodified one. The Km values of the modified sarcosine oxidase for sarcosine was nearly equal to or within 1.5 times of the Km value of the unmodified sarcosine oxidase. Furthermore, it has been shown that the modified sarcosine oxidase has at least either one of the reactivity to proline of 0.7% or less or Km value of 150 mM or more for L-proline as its property.

TABLE 5

| Modified one | Mutant | Acting upon proline | Km value (proline) | Km value (sarcosine) |
|---|---|---|---|---|
| SAOM1B | K89R | 0.70% | 151 mM | 3.4 mM |
| SAOM2B | V94G | 0.45% | 214 mM | 4.1 mM |
| SAOM3B | K322R | 0.42% | 122 mM | 4.7 mM |
| SAOM4B | V94G, E250Q | 0.58% | 213 mM | 3.4 mM |
| SAOM5B | V94G, E250Q, K89R | 0.55% | 198 mM | 3.3 mM |
| SAOM6B | K89R, V94G, S213P, E250Q | 0.54% | 210 mM | 3.5 mM |
| SAOM7B | K89R, V94G, M204A, S213P, E250Q | 0.41% | 203 mM | 3.4 mM |
| SAOM8B | K89R, V94G, N166K, M204A, S213P, E250Q | 0.41% | 205 mM | 3.4 mM |
| SAOM9B | K89R, V94G, N166K, M204A, S213P, E250Q, K322R | 0.28% | 202 mM | 4.4 mM |
| Unmodified (control) | — | 0.85% | 142 mM | 3.4 mM |

EXAMPLE 6B

Effect of Proline on Reagent for Measuring Creatinine

Effects of proline when various sarcosine oxidases obtained in Example 3B and Comparative Example 1 were applied to the reagent for measuring creatinine were evaluated. To 300 μL of 50 mM PIPES-NaOH buffer (pH 7.5) containing 10 U/mL sarcosine oxidase (prepared in Example 3 and Comparative Example 1), 1 mM dihydrogen disodium ethylenediamine tetraacetate, 50 mM sodium chloride, 0.1% (w/v) Triton X-100, 0.02% (w/v) 4-aminoantipyrine, 0.02% (w/v) TOOS (supplied from Dojindo Corporate), 100 U/mL creatinine amidohydrolase (CNH-211, supplied from Toyobo Co., Ltd.), 50 U/mL creatine amidinohydrolase (CRH-221, supplied from Toyobo Co., Ltd.), and 10 U/mL peroxidase (PEO-301, supplied from Toyobo Co., Ltd.), 10 μL of an aqueous solution of 5 mg/dL creatinine was added, reacted at 37° C., and changes of the absorbance at 546 nm were measured using Hitachi 17060 type automatic analyzer. Using an aqueous solution of 100 mg/dL L-proline instead of the aqueous solution of creatinine, the changes of the absorbance were measured by the same way as in the above. The effect of proline was calculated by a relative ratio (%) of an absorbance increase for 5 min of the reaction using L-proline as the substrate to an absorbance increase for 5 min of the reaction using creatinine as the substrate. The results are shown in Table 6. As is shown in Table 6, it has been confirmed that the effect of proline on the reagent is decreased by the use of the modified sarcosine oxidase of the present invention for the reagent for measuring creatinine.

TABLE 6

| Modified one | Mutant | Effect of proline |
|---|---|---|
| SAOM1B | K89R | 5.7% |
| SAOM2B | V94G | 3.6% |
| SAOM3B | K322R | 3.5% |
| SAOM4B | V94G, E250Q | 3.8% |
| SAOM5B | V94G, E250Q, K89R | 3.5% |
| SAOM6B | K89R, V94G, S213P, E250Q | 3.4% |
| SAOM7B | K89R, V94G, M204A, S213P, E250Q | 3.2% |
| SAOM8B | K89R, V94G, N166K, M204A, S213P, E250Q | 3.3% |
| SAOM9B | K89R, V94G, N166K, M204A, S213P, E250Q, K322R | 1.9% |
| Unmodified (control) | — | 7.2% |

EXAMPLE 7B

Effect of Proline on Reagent for Measuring Creatine

Effects of proline when various sarcosine oxidases obtained in Example 3B and Comparative Example 1 were applied to the reagent for measuring creatine were evaluated. To 300 μL of 50 mM PIPES-NaOH buffer (pH 7.5) containing 10 U/mL sarcosine oxidase (prepared in Example 3 and Comparative Example 1), 1 mM dihydrogen disodium ethylenediamine tetraacetate, 50 mM sodium chloride, 0.1% (w/v) Triton X-100, 0.02% (w/v) 4-aminoantipyrine, 0.02% (w/v) TOOS (supplied from Dojindo Corporate), 50 U/mL creatine amidinohydrolase (CRH-221, supplied from Toyobo Co., Ltd.), and 10 U/mL peroxidase (PEO-301, supplied from Toyobo Co., Ltd.), 10 μL of an aqueous solution of 5 mg/dL creatine was added, reacted at 37° C., and changes of the absorbance at 546 nm were measured using Hitachi 17060 type automatic analyzer. Using an aqueous solution of 100 mg/dL L-proline instead of the aqueous solution of creatine, the changes of the absorbance were measured by the same way as in the above. The effect of proline was calculated by a relative ratio (%) of an absorbance increase for 5 min of the reaction using L-proline as the substrate to an absorbance increase for 5 min of the reaction using creatine as the substrate. The results are shown in Table 7. As is shown in Table 7, it has been confirmed that the effect of proline on the reagent is decreased by the use of the modified sarcosine oxidase of the present invention for the reagent for measuring creatine.

TABLE 7

| Modified one | Mutant | Effect of proline |
|---|---|---|
| SAOM1B | K89R | 5.3% |
| SAOM2B | V94G | 3.1% |
| SAOM3B | K322R | 3.2% |
| SAOM4B | V94G, E250Q | 3.0% |
| SAOM5B | V94G, E250Q, K89R | 3.4% |
| SAOM6B | K89R, V94G, S213P, E250Q | 3.1% |
| SAOM7B | K89R, V94G, M204A, S213P, E250Q | 2.9% |
| SAOM8B | K89R, V94G, N166K, M204A, S213P, E250Q | 3.1% |
| SAOM9B | K89R, V94G, N166K, 204A, S213P, E250Q, K322R | 1.9% |
| Unmodified (control) | — | 7.0% |

The invention claimed is:

1. A modified sarcosine oxidase which is a protein comprising an amino acid sequence of SEQ ID NO: 1 in which valine at position 94 of SEQ ID NO: 1 is substituted with a different amino acid, and in which optionally at least one amino acid at a position selected from the group consisting of positions 82 to 92 and 354 to 366 of SEQ ID NO: 1 is substituted with a different amino acid, wherein the protein has sarcosine oxidase activity and a lowered action on L-proline compared with a sarcosine oxidase of SEQ ID NO: 1.

2. The modified sarcosine oxidase of claim 1, wherein valine at position 94 of SEQ ID NO: 1 is substituted with glycine.

3. The modified sarcosine oxidase of claim 1, wherein at least one amino acid at a position selected from the group consisting of positions 82 to 92 and 354 to 366 of SEQ ID NO: 1 is substituted with a different amino acid.

4. A modified sarcosine oxidase which is a protein comprising an amino acid sequence of SEQ ID NO: 1 in which valine at position 94 of SEQ ID NO: 1 is substituted with a different amino acid, and in which optionally at least one amino acid at a position selected from the group consisting of positions 89, 155, 166, 204, 213, 233, 240, 250, 322, and 364 of SEQ ID NO: 1 is substituted with a different amino acid, wherein the protein has sarcosine oxidase activity and a lowered action on L-proline compared with a sarcosine oxidase of SEQ ID NO: 1.

5. The modified sarcosine oxidase of claim 4, wherein lysine at position 89 is substituted with arginine.

6. The modified sarcosine oxidase of claim 4, wherein cysteine at position 155 is substituted with isoleucine.

7. The modified sarcosine oxidase of claim 4, wherein asparagine at position 166 is substituted with lysine.

8. The modified sarcosine oxidase of claim 4, wherein methionine at position 204 is substituted with alanine.

9. The modified sarcosine oxidase of claim 4, wherein serine at position 213 is substituted with proline.

10. The modified sarcosine oxidase of claim 4, wherein cysteine at position 233 is substituted with serine.

11. The modified sarcosine oxidase of claim 4, wherein asparagine at position 240 is substituted with tyrosine.

12. The modified sarcosine oxidase of claim 4, wherein glutamic acid at position 250 is substituted with glutamine.

13. The modified sarcosine oxidase of claim 4, wherein lysine at position 322 is substituted with arginine.

14. The modified sarcosine oxidase of claim 4, wherein alanine at position 364 is substituted with valine.

15. The modified sarcosine oxidase of claim 1, wherein the protein consists of the amino acid sequence of SEQ ID NO: 1 in which optionally at least one amino acid at a position selected from the group consisting of positions 82 to 92 and positions 354 to 366 of SEQ ID NO: 1 is substituted with a different amino acid.

16. The modified sarcosine oxidase of claim 4, wherein the protein consists of the amino acid sequence of SEQ ID NO: 1 in which optionally at least one amino acid at a position selected from the group consisting of positions 89, 155, 166, 204, 213, 233, 240, 250, 322, and 364 of SEQ ID NO: 1 is substituted with a different amino acid.

17. The modified sarcosine oxidase of claim 16, wherein lysine at position 89 is substituted with arginine, cysteine at position 155 is substituted with isoleucine, asparagine at position 166 is substituted with lysine, methionine at position 204 is substituted with alanine, serine at position 213 is substituted with proline, cysteine at position 233 is substituted with serine, asparagine at position 240 is substituted with tyrosine, glutamic acid at position 250 is substituted with glutamine, lysine at position 322 is substituted with arginine, and/or alanine at position 364 is substituted with valine.

18. The modified sarcosine oxidase of claim 1, wherein the protein comprises the amino acid sequence of SEQ ID NO: 1 in which valine at position 94 of SEQ ID NO: 1 is substituted with a different amino acid.

19. The modified sarcosine oxidase of claim 18, wherein valine at position 94 of SEQ ID NO: 1 is substituted with glycine.

* * * * *